US011919840B2

(12) United States Patent
Chrisman et al.

(10) Patent No.: US 11,919,840 B2
(45) Date of Patent: Mar. 5, 2024

(54) METHODS FOR OPERATING CONTINUOUS, UNMODULATED, MULTIPLE CATALYTIC STEP PROCESSES

(71) Applicant: T.EN Process Technology, Inc., Houston, TX (US)

(72) Inventors: Ray Chrisman, Midland, MI (US); Donald Bunning, South Charleston, WV (US); Mark Nunley, Charleston, WV (US); Brooke Albin, Charleston, WV (US); Michael Bradford, Charleston, WV (US); David James Schreck, Lake City, MN (US); Louis A. Kapicak, Cross Lanes, WV (US)

(73) Assignee: T.EN Process Technology, Inc., Houston, TX (US)

( * ) Notice: Subject to any disclaimer, the term of this patent is extended or adjusted under 35 U.S.C. 154(b) by 158 days.

(21) Appl. No.: 17/031,009

(22) Filed: Sep. 24, 2020

(65) Prior Publication Data
US 2021/0087127 A1   Mar. 25, 2021

Related U.S. Application Data

(60) Provisional application No. 62/905,068, filed on Sep. 24, 2019.

(51) Int. Cl.
*C07C 29/132* (2006.01)
*B01J 19/00* (2006.01)
*B01J 19/24* (2006.01)
*B01J 23/30* (2006.01)
*C07C 29/17* (2006.01)
*C07C 31/20* (2006.01)

(52) U.S. Cl.
CPC ......... *C07C 29/132* (2013.01); *B01J 19/0033* (2013.01); *B01J 19/004* (2013.01); *B01J 19/245* (2013.01); *B01J 23/30* (2013.01); *C07C 29/172* (2013.01); *B01J 2219/00033* (2013.01); *B01J 2219/0004* (2013.01); *B01J 2219/00243* (2013.01); *B01J 2523/69* (2013.01); *C07C 31/202* (2013.01)

(58) Field of Classification Search
None
See application file for complete search history.

(56) References Cited

U.S. PATENT DOCUMENTS

| 3,077,379 | A | 2/1963 | Pilloton |
| 3,193,347 | A | 7/1965 | Forward |
| 3,472,613 | A | 10/1969 | Hay et al. |
| 3,857,929 | A | 12/1974 | Quatrini et al. |
| 4,200,765 | A | 4/1980 | Goetz |
| 4,279,870 | A | 7/1981 | Natansohn |
| 4,765,834 | A | 8/1988 | Ananthapadmanabhan |
| 6,841,085 | B2 | 1/2005 | Werpy |
| 7,038,094 | B2 | 5/2006 | Werpy et al. |
| 7,094,932 | B2 | 8/2006 | Majerski |
| 7,335,800 | B2 | 2/2008 | Komplin |
| 7,762,715 | B2 | 7/2010 | Gordon |
| 8,014,880 | B2 | 9/2011 | Samardzija |
| 8,222,462 | B2 | 7/2012 | Kalnes et al. |
| 8,222,463 | B2 | 7/2012 | Kaines |
| 8,222,464 | B2 | 7/2012 | Kaines |
| 8,271,103 | B2 | 9/2012 | Hendler |
| 8,603,198 | B2 | 12/2013 | Gordon |
| 8,673,129 | B2 | 3/2014 | Gordon |
| 8,816,068 | B2 | 8/2014 | Kuusisto |
| 8,877,985 | B2 | 11/2014 | Powell |
| 8,981,135 | B2 | 3/2015 | Gordon et al. |
| 9,069,345 | B2 | 6/2015 | McCready |
| 9,302,965 | B1 | 4/2016 | Van Der Heide et al. |
| 9,440,897 | B2 | 9/2016 | Lange et al. |
| 9,447,347 | B2 | 9/2016 | Chheda et al. |
| 9,656,933 | B2 | 5/2017 | Van Der Heide et al. |
| 9,745,234 | B2 | 8/2017 | Van Der Heide et al. |
| 9,884,798 | B2 | 2/2018 | Van Der Heide et al. |

(Continued)

FOREIGN PATENT DOCUMENTS

| CN | 102643165 | A | * | 8/2012 |
| NL | 2014119 | A | | 9/2016 |

(Continued)

OTHER PUBLICATIONS

Schwengber, C. A. et al. "Methane dry reforming using Ni/Al2O3 catalysts: Evaluation of the effects of temperature, space velocity and reaction time" Journal of Environmental Chemical Engineering 4 (2016) 3688-3695 (Year: 2016).*

Iglesia, E. "Design, synthesis, and use of cobalt-based Fischer-Trospch synthesis catalysts" Applied Catalysis A: General 161 (1997) 59-78 (Year: 1997).*

Ismail et al., "Aqueous-Only, Green Route to Self-Healable, UV-Resistant, and Electrically Conductive Polyurethane/Graphene/Lignin Nanocomposite Coatings", "ACS Sustainable Chem. Eng.", Feb. 15, 2017, pp. 3148-3157, vol. 5.

Makino et al., "Recovery and Recycling of Tungsten by Alkaline Leaching of Scrap and Charged Amino Group Assisted Precipitation", "ACS Sustainable Chem Eng", Jan. 19, 2018, pp. 4246-4252, vol. 6.

(Continued)

*Primary Examiner* — Medhanit W Bahta
(74) *Attorney, Agent, or Firm* — Locke Lord LLP; Gabrielle L. Gelozin

(57) ABSTRACT

Control methods are disclosed for continuous, unmodulated, multiple catalytic conversion step processes using at least two catalysts, a first catalyst and a second catalyst, that accommodate changes in the performance of each catalyst and the relative performances of the catalysts. In the methods, certain process parameters are used in a manner that is indicative of changes in catalyst performance, and the control methods provide for adjustment of at least one of: the absolute amount of catalytically active species and relative amounts of each of the first catalyst and second catalyst and at least one of the rate of feed or concentration of the raw material to the reaction zone.

18 Claims, No Drawings

(56) References Cited

U.S. PATENT DOCUMENTS

| | | |
|---|---|---|
| 10,035,744 B2 | 7/2018 | Huizenga et al. |
| 10,081,584 B2 | 9/2018 | Fischer et al. |
| 10,093,602 B2 | 10/2018 | Van Der Heide et al. |
| 10,125,071 B2 | 11/2018 | Van Der Heide et al. |
| 10,131,600 B2 | 11/2018 | Van Der Waal et al. |
| 10,138,184 B2 | 11/2018 | Van Der Waal et al. |
| 10,221,116 B2 | 3/2019 | Huizenga et al. |
| 10,233,138 B2 | 3/2019 | Van Der Waal |
| 10,246,390 B2 | 4/2019 | Huizenga et al. |
| 10,266,470 B2 | 4/2019 | Huizenga et al. |
| 10,294,180 B2 | 5/2019 | Van Der Waal et al. |
| 10,294,181 B2 | 5/2019 | Chewter et al. |
| 10,308,577 B2 | 6/2019 | Perez Golf et al. |
| 10,369,550 B2 | 8/2019 | Edulji et al. |
| 10,450,249 B2 | 10/2019 | Van Der Heide et al. |
| 10,450,255 B2 | 10/2019 | Muthusamy |
| 10,464,870 B2 | 11/2019 | Liu et al. |
| 10,478,809 B2 | 11/2019 | Geyer et al. |
| 10,519,086 B2 | 12/2019 | Muthusamy et al. |
| 10,556,226 B2 | 2/2020 | Liu et al. |
| 10,562,012 B2 | 2/2020 | Colijn et al. |
| 10,647,646 B2 | 5/2020 | Van Der Heide |
| 10,647,647 B2 | 5/2020 | Van Der Heide et al. |
| 10,654,782 B2 | 5/2020 | Muthusamy et al. |
| 10,752,567 B2 | 8/2020 | Muthusamy et al. |
| 11,008,269 B2 | 5/2021 | Dekker et al. |
| 11,059,768 B2 | 7/2021 | Van Der Waal et al. |
| 2008/0109100 A1 | 5/2008 | Macharia et al. |
| 2011/0312487 A1 | 12/2011 | Chen et al. |
| 2011/0312488 A1 | 12/2011 | Chen et al. |
| 2014/0042358 A1 | 2/2014 | Suppes |
| 2014/0259886 A1 | 9/2014 | Budaragu et al. |
| 2015/0329449 A1 | 11/2015 | Schreck et al. |
| 2016/0186072 A1* | 6/2016 | Lehoux ............... C12P 3/00 435/167 |
| 2016/0207856 A1 | 7/2016 | Van Der Heide et al. |
| 2016/0304423 A1 | 10/2016 | Schreck et al. |
| 2017/0001932 A1 | 1/2017 | Van Der Heide et al. |
| 2017/0210687 A1 | 7/2017 | Liu et al. |
| 2017/0305823 A1 | 10/2017 | Fischer et al. |
| 2017/0349513 A1 | 12/2017 | Schreck et al. |
| 2018/0016214 A1 | 1/2018 | Ma |
| 2018/0086681 A1 | 3/2018 | Schreck et al. |
| 2018/0142593 A1 | 5/2018 | Wang et al. |
| 2018/0150037 A1 | 5/2018 | Amrit et al. |
| 2018/0187219 A1 | 7/2018 | Van Der Heide |
| 2018/0201559 A1 | 7/2018 | Martin et al. |
| 2018/0272319 A1 | 9/2018 | Muthusamy |
| 2018/0273452 A1 | 9/2018 | Van Der Bijl et al. |
| 2018/0273453 A1 | 9/2018 | Van Der Bijl et al. |
| 2018/0297920 A1 | 10/2018 | Muthusamy et al. |
| 2018/0362424 A1 | 12/2018 | Chewter et al. |
| 2018/0362425 A1 | 12/2018 | Van Der Heide et al. |
| 2018/0364747 A1* | 12/2018 | Charr ............... B01J 19/0033 |
| 2019/0010103 A1 | 1/2019 | Osmundsen et al. |
| 2019/0010104 A1 | 1/2019 | Holm et al. |
| 2019/0039979 A1 | 2/2019 | Van Der Heide et al. |
| 2019/0047929 A1 | 2/2019 | De Vlieger et al. |
| 2019/0084907 A1 | 3/2019 | Huizenga et al. |
| 2019/0202764 A1 | 7/2019 | Fischer et al. |
| 2019/0256446 A1 | 8/2019 | Muthusamy et al. |
| 2019/0330417 A1 | 10/2019 | Ren et al. |
| 2019/0359548 A1 | 11/2019 | Liu et al. |
| 2020/0109098 A1 | 4/2020 | Muthusamy |
| 2020/0325090 A1 | 10/2020 | Fischer et al. |
| 2020/0377438 A1 | 12/2020 | Huizenga et al. |
| 2020/0406237 A1 | 12/2020 | Singh et al. |

FOREIGN PATENT DOCUMENTS

| | | | |
|---|---|---|---|
| NL | 2014120 A | 9/2016 | |
| WO | 2015154258 A1 | 10/2015 | |
| WO | 2016001136 A1 | 1/2016 | |
| WO | 2016114658 | 7/2016 | |
| WO | 2016114659 A1 | 7/2016 | |
| WO | 2016114660 A1 | 7/2016 | |
| WO | 2016114661 A1 | 7/2016 | |
| WO | 2016196752 A1 | 12/2016 | |
| WO | 2017001382 A1 | 1/2017 | |
| WO | 2017055285 A1 | 4/2017 | |
| WO | 2017070067 | 4/2017 | |
| WO | WO-2017055289 A1 * | 4/2017 | ........... C07C 29/132 |
| WO | 2017085234 | 5/2017 | |
| WO | 2017097839 A1 | 6/2017 | |
| WO | 2017137355 A1 | 8/2017 | |
| WO | 2017202731 A1 | 11/2017 | |
| WO | WO 2018024787 A1 | 2/2018 | |
| WO | 2018104508 A1 | 6/2018 | |
| WO | 2020055796 A1 | 3/2020 | |
| WO | 2020055831 A1 | 3/2020 | |
| WO | 2020182456 A1 | 9/2020 | |
| WO | WO-2020182456 A1 * | 9/2020 | |
| WO | 2020212542 A1 | 10/2020 | |
| WO | 2021058805 A1 | 4/2021 | |
| WO | 2021058808 A1 | 4/2021 | |
| WO | 2021122853 A1 | 6/2021 | |

OTHER PUBLICATIONS

Mesbah et al., "Model Predictive Control of an Integrated Continuous Pharmaceutical Manufacturing Pilot Plant", "Organic Process Research and Development", May 17, 2017, pp. 844-854, vol. 21, No. 6, Publisher: ACS Publications.

Ogi et al., "Facile and Efficient Removal of Tungsten Anions Using Lysine-Promoted Precipitation for Recycling High-Purity Tungsten", "ACS Sustainable Chem Eng.", Feb. 18, 2017, pp. 3141-3147, vol. 5.

Jifeng Pang et al, "Catalytic conversion of cellulosic biomass to ethylene glycol: Effects of inorganic impurities in biomass", "Bioresource Technology", 2014, pp. 424-429, vol. 175, Publisher: Elsevier Ltd.

Pfrepper et al., "Continuous on-line chromatography of short lived isotopes of tungsten as homolog of seaborgium (element 106)", "RAdiochim Acta", 3/3/200, pp. 273-278, vol. 88.

Sadighi-Bonabi et al., "Laser induced sonofusion: A new road toward thermonuclear reactions", "AIP Advances", Mar. 29, 2016, vol. 6, No. 3, Publisher: AIP Publishing.

Thanekar et al., "Application of Hydrodynamic Cavitation Reactors for Treatment of Wastewater Containing Organic Pollutants: Intensification Using Hybrid Approaches", "Fluids", Nov. 23, 2018, vol. 3, No. 98.

Wu et al., "Tungsten Recovery from Spent SCR Catalyst Using Alkaline Leaching and Ion Exchange", "Minerals", Oct. 17, 2016, vol. 6, No. 107.

Xi et al., "Production of Ethylene Glycol and Its Monether Derivative from Cellulose", "ACS Sustainable Chem. Eng.", Sep. 2, 2014, pp. 2355-2362, vol. 2.

Zhang et al., "A Novel Process for Tungsten Hydrometallurgy Based on Direct Solvent Extraction in Alkaline Medium", "Hydrometallurgy", Jan. 1, 2016, pp. 233-237, vol. 165.

Zhao et al., "Ethylene Glycol Production from Glucose Over W—Ru Catalysts: Maximizing Yield by Kinetic Modeling and Simulation", Jun. 1, 2017, pp. 2072-2080, vol. 63, No. 6, Publisher: AIChE Journal.

Wikipedia, "Glucose", Jun. 13, 2019.

Wikipedia, "Hydroxyacetone", Aug. 19, 2018.

Yazdani et al., "Glucose hydrogenolysis over Cu—La2oc/AlcO3: Mechanistic insights", "Molecular Catalysis", Jan. 1, 2019, pp. 138-145, vol. 466.

Matsuoka et al., "Retro=aldol-type fragmentation of reducing sugars preferntially occuriing in polyether at high temperature: Role of the ehter oxygen as a base catalyst", Journal of Analytical and Applied Pyrolysis, Jan. 1, 2012, pp. 24-32, vol. 93.

* cited by examiner

METHODS FOR OPERATING CONTINUOUS, UNMODULATED, MULTIPLE CATALYTIC STEP PROCESSES

CROSS-REFERENCE TO RELATED APPLICATION(S)

This application claims the benefit under 35 U.S.C. § 119(e) to U.S. Provisional Application 62/905,068, filed Sep. 24, 2019, and entitled "METHODS FOR OPERATING CONTINUOUS, UNMODULATED, MULTIPLE CATALYTIC STEP PROCESSES FIELD OF THE INVENTION," which is hereby incorporated herein by reference in its entirety for all purposes.

TECHNICAL FIELD

This invention pertains to methods for operating chemical conversion processes using two or more sequential catalytic conversions, especially to such processes where the flow between catalytic conversions is unmodulated. The methods of this invention include, but are not limited to, predictive control methods and design space methods.

BACKGROUND

Catalytic processes are in commercial use for the production of chemicals, pharmaceuticals, fuels, polymers and the like. In some of these processes, the feedstock, or raw material must undergo two or more catalytic reactions, or multistep processes, to provide the sought product. The raw material is first converted to an intermediate and then one or more conversion steps occur to provide the sought product.

Conventionally, these multistep processes proceed in distinct steps, that is, the raw material is subjected to catalytic conditions to produce an intermediate, the intermediate is recovered and then subjected to a second catalytic step to produce a chemical product. For purposes herein, this is referred to as a modulated cascade process. Thus, each step of the modulated cascade process can be controlled to reflect, among other things, the process conditions desired to achieve conversion efficiency and selectivity.

Most catalysts are subject to changes in performance due to deactivation and aging or physical loss. Also, in some instances, the production of by-products and other loss of raw material or intermediate, as the case may be, is affected directly or indirectly by the condition of the catalyst. For a single catalytic conversion processes or modulated cascade processes, the optimization of conditions can take into account the condition of the catalyst used in a single conversion. Thus, when adjustments of temperature, pressure, feed rates of reactants, residence time, adjuvants, pH and other controllable process variables are made, the operator has reasonable certainty as to the effect of the change. Hence, the multistep processes offer the benefit of controlling the overall process on a step-wise basis and avoiding confounding the control of one catalytic process with that of another catalytic process.

The step-by-step control of modulated, cascade processes, especially with the recovery of intermediates between steps, increases production costs. Operating the multi-step process as an unmodulated cascade process could provide economic benefits, especially if the multiple steps were under a unified control system. By unmodulated cascade process it is meant that separate reaction zones exist and an intermediate-containing liquid stream from a first reaction zone passes to a subsequent reaction zone where it is reacted without removing intermediate. The subsequent reaction zone can be the next reaction zone or a later reaction zone in flow sequence.

In addition to modulated cascade processes, multistep processes have been proposed that occur in a single reaction zone ("single pot"). These single pot processes are often unavoidable where the intermediates can react to provide undesirable by-products. Thus, to achieve viable economics, the intermediates are quickly subjected to the next catalytic reaction in an effort to mitigate the production of by-products. One such process is the conversion of sugars to ethylene glycol and propylene glycol by sequential retro-aldol and hydrogenation steps. The retro-aldol step generates, for example, glycol aldehyde, which when hydrogenated provides ethylene glycol. On the other hand, since glycol aldehyde is highly reactive, it can also react without the presence of catalyst to by-products, e.g., 1,2-butanediol. In these latter multi-step processes, it has been proposed to either conduct the multiple reactions in a single vessel or in sequential vessels, the first containing the first catalyst and being substantially devoid of the second catalyst.

Typical process control focuses on conversion and selectivity to the sought product and manipulative inputs such as one or more of feed rate, concentration of the raw material in the feed, temperature, pressure, residence time, pH and the concentration of adjuvants, are inputs to the process control, and one or more of the manipulative inputs are adjusted to provide an operation that meets the process objective. Changes in catalyst performances and relative performances of the catalysts are confounding factors in process control, and thus adjustments made in response to a manipulative input, which are thought to improve conversion and selectivity, can result in the operation becoming unstable due to the performance of the catalysts. Additionally, even when the manipulative inputs indicate no operational problem, the performance of one or more of the catalysts could be deteriorating to the point that destabilization occurs.

A desire thus exists to provide methods for controlling continuous, unmodulated, multiple catalytic conversion step processes to accommodate changes in the performance of each catalyst and the relative performances of the catalysts. Moreover, it is desired that such methods use input parameters that can be reasonably obtained from the process, especially input parameters that can be ascertained relatively quickly to provide real-time data regarding the operation of the process.

BRIEF SUMMARY

By this invention control methods are provided to perform continuous, unmodulated, multiple catalytic conversion step processes using at least two catalysts, a first catalyst and a second catalyst, that accommodate changes in the performance of each catalyst and the relative performances of the catalysts. The processes convert in a medium at least one raw material to a desired chemical product including the contact of the raw material with a first catalyst to provide an intermediate and then contact of the intermediate with a second catalyst to provide the chemical product. Although the discussion herein references two catalysts, that is for purposes of ease of understanding. The methods of this invention are equally applicable to processes where three or more sequential catalytic reactions are used. The methods of this invention also encompass processes where one or more non-catalytic reactions occur before, between or after two catalytic reactions. For instance, the first catalytic reaction can provide an intermediate that reacts with another chemical contained in the reaction system to form non-catalytically a second intermediate which in turn is catalytically reacted to the sought chemical product. In the methods, certain process parameters are used in a manner that is indicative of catalyst performance, and the control methods provide for adjustment of at least one of: the absolute amount of catalytically active species and relative amounts of each of the first catalyst and second catalyst and the rate of feed and concentration of the raw material to the reaction zone.

The methods of this invention comprise determining from the effluent from the second catalyst ("withdrawn medium"), (I) using the rate and concentration of a raw material in the feed to the process, the conversion efficiency of the process to the desired product, and (II) at least one of concentration of at least one by-product in the withdrawn medium, concentration of intermediate in the withdrawn medium and, if used, concentration of at least one tracer. Both (I) and (II) can rely upon conventional analyses of samples of the raw material feed to and product streams from the multiple catalytic conversion step process, and generally analytical equipment for determining concentrations of the recited components can provide near real-time data, e.g., within 30, and often within 10 or 5, minutes of sampling.

Without wishing to be limited by theory, it is believed that the concentration of at least one of by-product, intermediate and tracer, are selectively indicative of a change in performance of one of the catalysts. In some instances, a by-product or tracer is more sensitive to the reaction conditions than the products themselves. For instance, in the retro-aldol/hydrogenation conversion of glucose to ethylene glycol, an increase in hydroxyacetone presages an observable decrease in selectivity to ethylene glycol. The term absolute amount of catalytically active species in a reaction zone is used herein refers to the effectiveness of the catalyst in that reaction zone and does not necessarily relate to the mass of the catalysts. The absolute amount of catalytically active species can be based upon the performance of the catalyst and can be a relative relationship. Thus, the absolute amount of catalytically active species can be altered without changing the mass of that catalyst by, for instance, deactivation, conversion to inactive or less active molecules, promoter addition, or poisoning, or the absolute amount of catalytically active species can be altered by the addition or removal of that catalyst from the reaction zone. Adjustments can be made to one of the catalysts to provide a balance of their performances or the feed rate can be reduced to accommodate the effective capacity of the deteriorated catalyst. Adjustments to the catalysts include, but are not limited to, the addition of more catalyst to the reaction zone and chemical modifications of a catalyst. Chemical modifications include, but are not limited to, the addition of promoters or poisons to the reaction zone to selectively affect the activity of one of the catalysts. It is understood that reaction parameters can also affect the performance of a catalyst. For instance, changes in temperature can affect the kinetics of the catalytic reaction. For purposes herein, such parameter changes are not considered to change the absolute amount of catalytically active species although the catalyst may be more or less active after the change of the parameter. Where one of the catalysts is homogeneous or a finely dispersed heterogeneous catalyst and present throughout the reaction zone, addition or removal of such catalyst can occur with medium added to or withdrawn from the reaction zone to provide the desired activity in the reaction zone.

The control method of this invention can, if desired, be incorporated into more expansive control systems for the process which systems can be design space systems (DSC) or model predictive control systems (MPC), both of which are well known in the art. In a DSC, boundary conditions, or windows, are predetermined and operation within the windows is considered to be under control. In an MPC, dynamic process models, which are often empirically generated, take into account current control status as well as its effect on the process in the future. Control actions can be taken based upon the predictive models in anticipation of future events.

One broad aspect of this invention pertains to predictive control methods for operating a continuous, unmodulated, sequential, multi-catalytic reaction process wherein each catalyst is subject to changes in performance in the course of the process, the process to which the methods of this invention pertain comprises (i) continuously or intermittently introducing at a feed rate and concentration at least one raw material, and optionally a tracer precursor, into a reaction zone containing a medium, (ii) maintaining the reaction zone under catalytic conversion conditions suitable for the first catalytic conversion to produce a medium containing the intermediate, said conditions including temperature, pressure, residence time, concentration of the first catalyst, and, optionally, pH and adjuvants, (iii) contacting the medium containing the intermediate with the second catalyst under conditions suitable for the other conversion to produce the chemical product, said conditions including temperature, pressure, residence time, concentration of the second catalyst, and, optionally, pH and adjuvants, and (iv) continuously or intermittently withdrawing medium containing chemical product from contact with the second catalyst at a rate to provide a continuous process;

wherein at least one byproduct is produced, and wherein the catalytic activity of at least one of the first catalyst and second catalyst is subject to performance change during the continuous operation, said control method comprising:

(a) continuously or intermittently inputting predetermined process parameters from the process operation into a model predictive control apparatus having a control model;

(b) adjusting, as necessary to meet a desired process objective, manipulative inputs to the process; and, optionally (c) adjusting the control model, wherein:

(A) in element (a) the predetermined process parameters inputted comprise (I) the rate and concentration of feed of raw material in step (i) and the conversion efficiency of the raw material to the chemical product and (II) at least one of:

concentration of at least one by-product in the withdrawn medium, concentration of intermediate in the withdrawn medium and concentration of at least one tracer in the withdrawn medium to reflect in control model data pertaining to the performances of the catalysts; and (B) adjusting, as necessary to meet a desired process objective, at least one of: (I) the absolute amount of catalytically active species and relative amounts of each of the first catalyst and second catalyst, and (II) at least one of the rate of feed of the raw material and its concentration to the reaction zone as manipulative inputs.

In a preferred embodiment of this first broad aspect of the invention, the reaction process comprises the catalytic conversion of sugars to at least one of ethylene glycol and propylene glycol by sequential retro-aldol catalytic conversion (first catalyst) to intermediates and catalytic hydrogenation (second catalyst) of intermediates to at least one of ethylene glycol and propylene glycol ("lower glycol"). In many instances, the retro-aldol catalyst is homogeneous and the hydrogenation catalyst is heterogeneous. This process is complex and is subject to many reactions, catalytic and non-catalytic. For instance, sugars can isomerize, and intermediates can react to by-products, all of which adversely affects selectivity to the sought lower glycol. The desired process objective is often the selectivity of conversion to either ethylene glycol or propylene glycol, and in some instances, the selectivity to the total of ethylene glycol and propylene glycol ("total lower glycol") is greater than about 75 mass percent based upon the mass of the feed. The by-products for the method include one or more of 1,2-butanediol, hydroxyacetone and one or more itols, pH, and, if used, the preferred tracer precursor is one or more ketone of 3 to 6, preferably 4 to 6, carbons and the tracer is unreacted ketone and the reaction products of the ketone. The predictive control model preferably determines pH of the effluent and pH is inputted into the model. As acids can be by-products of this process, the pH can be a useful input. The reaction process can be a cascade process or a single pot process.

A second broad aspect of this invention pertains to design space methods for operating a continuous, unmodulated, sequential, multi-catalytic reaction process wherein each catalyst is subject to changes in performance in the course of the process, which methods adjust manipulative inputs to provide outputs within predetermined ranges. The process to which the methods of this invention pertain comprises:

(i) continuously or intermittently introducing at a feed rate and concentration at least one raw material, and optionally a tracer precursor, into a reaction zone containing liquid medium, (ii) maintaining the reaction zone under catalytic conversion conditions suitable for the first catalytic conversion to produce a liquid medium containing the intermediate, said conditions including temperature, pressure, residence time, concentration of the first catalyst, and, optionally, pH and adjuvants, (iii) contacting the liquid medium containing the intermediate with the second catalyst under conditions suitable for the other conversion to produce the chemical product, said conditions including temperature, pressure, residence time, concentration of the second catalyst, and, optionally, pH and adjuvants, and (iv) continuously or intermittently withdrawing liquid medium containing chemical product from contact with the second catalyst at a rate to provide a continuous process; wherein at least one byproduct is produced, and wherein the catalytic activity of at least one of the first catalyst and second catalyst is subject to performance change during the continuous operation, The method comprises:

(a) continuously or intermittently comparing predetermined process parameters from the process operation to predetermined windows for such operation; and (b) adjusting, as necessary to meet a desired process objective, manipulative inputs to the process, wherein in element (a) the predetermined process parameters inputted comprise (I) the rate and concentration of feed of raw material in step (i) and the conversion efficiency of the raw material to the chemical product and (II) at least one of:

concentration of at least one by-product in the withdrawn liquid medium, concentration of intermediate in the withdrawn liquid medium and concentration of at least one tracer in the withdrawn liquid medium, wherein in element (b) adjustment is made to at least one of: (I) the absolute amount of catalytically active species and relative amounts of each of the first catalyst and second catalyst, and (II) at least one of the rate of feed of the raw material and its concentration to the reaction zone as the manipulative inputs.

In a preferred embodiment of this first broad aspect of the invention, the reaction process comprises the catalytic conversion of sugars to at least one of ethylene glycol and propylene glycol by sequential retro-aldol catalytic conversion (first catalyst) to intermediates and catalytic hydrogenation (second catalyst) of intermediates to at least one of ethylene glycol and propylene glycol ("lower glycol"). In many instances, the retro-aldol catalyst is homogeneous and the hydrogenation catalyst is heterogeneous. This process is complex and is subject to many reactions, catalytic and non-catalytic. For instance, sugars can isomerize, and intermediates can react to by-products, all of which adversely affects selectivity to the sought lower glycol. The desired process objective is often the selectivity of conversion to either ethylene glycol or propylene glycol, and in some instances, the selectivity to the total of ethylene glycol and propylene glycol ("total lower glycol") is greater than about 75 mass percent based upon the mass of the feed. The by-products for the method include one or more of 1,2-butanediol, hydroxyacetone and one or more itols, pH, and, if used, the preferred tracer precursor is one or more ketone of 3 to 6, preferably 4 to 6, carbons and the tracer is unreacted ketone and the reaction products of the ketone. The predictive control model preferably determines pH of the effluent and pH is inputted into the model. As acids can be by-products of this process, the pH can be a useful input. The reaction process can be a cascade process or a single pot process.

While multiple embodiments are disclosed, still other embodiments of the disclosure will become apparent to those skilled in the art from the following detailed description, which shows and describes illustrative embodiments of the invention. As will be realized, the disclosure is capable of modifications in various obvious aspects, all without departing from the spirit and scope of the disclosure. Accordingly, the drawings and detailed description are to be regarded as illustrative in nature and not restrictive.

DETAILED DESCRIPTION

All patents, published patent applications and articles referenced herein are hereby incorporated by reference in their entirety.

Definitions

As used herein, the following terms have the meanings set forth below unless otherwise stated or clear from the context of their use.

Where ranges are used herein, the end points only of the ranges are stated so as to avoid having to set out at length and describe each and every value included in the range. Any appropriate intermediate value and range between the recited endpoints can be selected. By way of example, if a range of between 0.1 and 1.0 is recited, all intermediate values (e.g., 0.2, 0.3, 0.63, 0.815 and so forth) are included as are all intermediate ranges (e.g., 0.2-0.5, 0.54-0.913, and so forth).

The use of the terms "a" and "an" is intended to include one or more of the element described.

Admixing or admixed means the formation of a physical combination of two or more elements which may have a uniform or non-uniform composition throughout and includes, but is not limited to, solid mixtures, solutions and suspensions.

Bio-sourced carbohydrate feedstock means a product that includes carbohydrates sourced, derived or synthesized from, in whole or in significant part, to biological products or renewable agricultural materials (including, but not limited to, plant, animal and marine materials) or forestry materials.

By-products are incidental or secondary products made in the manufacture of the sought product and include the incidental or secondary products and intermediates to these products and include reaction products from the sought product. By-products do not include intermediates to the sought product. By way of example, in the catalytic conversion of glucose to ethylene glycol, any unreacted glycol aldehyde would not be a by-product but hydroxyacetone would be a byproduct, even though either might be able to be further reacted under the conditions of the reaction. Other by-products include, but are not limited to, mannitol, sorbitol, glycerin, 1,2-butanediol, erythritol, threitol, organic acids, and gases.

Catalyst means a heterogeneous or homogeneous catalyst. For purposes herein, catalysts that behave as if they are dissolved in the media, e.g., a colloidal suspension, are considered to be homogeneous catalysts regardless of whether or not they are dissolved. A catalyst can be enzymatic or can be inorganic and contain one or more catalytic metals, and for heterogeneous catalysts, include supports, binders and other adjuvants. Catalytic metals are metals that are in their elemental state or are ionic or covalently bonded. The term catalytic metals refers to metals that are not necessarily in a catalytically active state, but when not in a catalytically active state, have the potential to become catalytically active. Catalytic metals can provide catalytic activity or modify catalytic activity such as promotors, selectivity modifiers, and the like.

Catalytic activity or performance refers to the extrinsic activity of a catalyst in the reaction zone. Thus, the factors that affect catalyst activity include the condition of the catalyst per se, but also include its deployment in the reaction zone. For example, if a portion of the catalyst is physically occluded in the reaction zone, it is relatively unavailable for effecting the sought catalytic conversion even though it may be active per se. Mixing or other means of redistribution to make the catalyst surface accessible would thus improve the extrinsic catalytic activity.

A change in catalytic activity can result from a change in the catalyst per se such as a chemical change, physical degradation, redistribution of components on the catalyst, loss of catalytically-active species from the catalyst, or poisoning or other effect from a component that become deposited or reacted during the course of the reaction. A change in catalytic activity can also be caused by the environment around the catalyst where the catalyst itself may be relatively unchanged, e.g., through steric effects or reactions or complexing with the components to be catalytically converted. Therefore, an increase or decrease in catalytic activity can, but does not necessarily result from an increase or decrease in the mass of catalyst per unit volume.

A chemical product is a chemical compound or mixture of chemical compounds that is in the effluent from contact with the second catalyst in the reaction zone. It can be a marketable product or a feed stock for further reaction. Thus, the term chemical product is used to designate the composition in a location in the methods of the invention.

Commencing contact means that a fluid starts a contact with a component, e.g., a medium containing a homogeneous or heterogeneous catalyst, but does not require that all molecules of that fluid contact the catalyst.

Conversion efficiency is the mass percent of a raw material that is converted in the process to chemical product.

First catalyst and second catalyst mean two different catalysts and the terms are not intended to exclude the presence of other catalysts, which other catalysts may be intermediate in the reaction process to the first and second catalyst, or may be in the reaction process before the first catalyst or after the second catalyst. The significance of the second catalyst is that is where certain input values for the control system are determined. For instance, a feed may first contact a first catalyst to provide an intermediate and then contacted with another catalyst that can convert the intermediate to a further intermediate. This further intermediate can be converted over the second catalyst to the chemical product.

Hydraulic distribution means the distribution of an aqueous solution in a vessel including contact with any catalyst contained therein.

Intermediate means a compound that can be further reacted under the conditions in the reaction zone to the sought product. As defined herein, an intermediate to a by-product is itself deemed to be a by-product.

Intermittently means from time to time and may be at regular or irregular time intervals.

Input values mean input information from the process for the control method. The inputs can be manipulative inputs, sometimes referred to as independent variables, which means that the value being reported is subject to control such as temperature. The inputs can be process parameters, sometimes referred to as dependent variables, which means that the determined value is resulting from multiple manipulative variables in the process. For instance, concentration of an intermediate, by-product or chemical product is the result of the combined set of process conditions. An input value can be from one or two or more manipulative inputs and process parameter inputs and can require calculations. For example, conversion efficiency can be determined from raw material concentration in the feed and the feed rate to the reaction zone and from the concentration of the chemical product in the effluent from the reaction zone and the flow rate of the effluent.

Itols are polyhydric alcohols with each carbon having a hydroxyl group, e.g., sugar alcohols.

The medium is a gas, liquid, supercritical or mixed phase fluid containing the raw materials, intermediates, by-products and chemical products that passes through the reaction zone. The medium can be formed using an inert, e.g., a solvent or suspension medium for liquid media, or the raw materials, intermediates, by-products and chemical products can form all or a portion of the medium. The medium can contain other components such as buffers and other adjuvants.

pH control agents mean one or more of buffers and acids or bases.

A process objective can be a single or plurality of objectives sought for operation of the process. For instance, a process objective may be to maximize conversion efficiency to the chemical product or may be to maximize production rate of the chemical product. The objectives can be primary and secondary such as maximizing production rate subject to maintaining the concentration of a by-product below a certain level.

The term raw material is used to indicate one or more reactant that are added to the reaction zone in the process and is not intended to reflect on purity or need for refining. The raw material can be a product from another chemical or biochemical process. Since reactants include intermediates, the term raw material thus facilitates understanding.

A reaction zone is the volume that contains the first and second catalyst and can be a single vessel or plural vessels, or reactors. A reaction zone, while containing both the first and second catalyst, may have regions containing only one of the catalysts or rich in one of the catalysts.

A reactor can be one or more vessels in series or in parallel and a vessel can contain one or more zones. A reactor can be of any suitable design for continuous operation including, but not limited to, tanks and pipe or tubular reactors and can have, if desired, fluid mixing capabilities. Types of reactors include, but are not limited to, laminar flow reactors, fixed bed reactors, slurry reactors, fluidized bed reactors, moving bed reactors, simulated moving bed reactors, trickle-bed reactors, bubble column and loop reactors.

A tracer precursor is a chemical compound that is capable of being catalytically converted by only the first catalyst or the second catalyst. A tracer is a compound derived from the tracer precursor that is contained in the withdrawn liquid medium. The tracer can be unreacted tracer precursor or a reaction product of the tracer precursor.

Discussion

The methods of this invention for operating continuous, unmodulated, sequential, multi-catalytic reaction processes address the changes in catalytic activity of the catalysts and their relative performances during the course of the processes. The methods involve using certain process parameters in control systems and then adjusting to meet process objectives at least one of: (I) the absolute amount of catalytically active species and relative amounts of each of the first catalyst and second catalyst, and (II) at least one of the rate of feed of the raw material and its concentration to the reaction zone as manipulative inputs. The control system hardware used is not critical to the disclosed methods, and individual manipulative input adjustment to set points, design space control systems and model predictive control systems and the like can be used.

Design space and model predictive control are well known and are multivariate. The former is based upon models and manipulative inputs values are maintained to windows of acceptable operation. Where manipulative inputs are interrelated, the design space control systems can be designed with predictive models such that adjustments in one manipulative input coincide with adjustments in one or more other manipulative inputs. The later considers not only the instantaneous state of the process but also the future state of the process. The models can be developed on, for instance, a linear or quadratic models. These models can be derived from empirical data and the performance of the process with respect to process objectives. With respect to model predictive control, data from the process can be used to refine the future predictive aspect of the models. The control systems can be open loop or closed loop, and where closed loop, the loop can be the entire plant or a portion thereof. As this disclosure pertains to an unmodulated, sequential catalytic conversion, the control systems address at least the reaction zone.

With any process control system, the critical issue is the selection of the inputs to be used, and how those inputs are to be reflected in the control of the process. It is that selection and the resultant control that constitutes this invention. It is apparent that once understanding the invention, a control engineer of ordinary skill in the art would be enabled to implement the invention in a control system.

The methods disclosed herein are broadly applicable to chemical processes using continuous, unmodulated, sequential, multi-catalytic reactions where the catalysts are subject to changes in performance in the course of the process. The processes can be said to have a single reaction zone within which at least two catalytic conversions occur. The catalytic conversions can occur in different or the same region of the reaction zone and the reaction zone can comprise one or more vessels in parallel or in series provided that the flow is substantially unmodulated.

The first and second catalysts can be homogeneous or heterogeneous catalysts or one may be homogeneous and the other heterogeneous. Where both are heterogeneous, the catalysts may be located in separate regions of the reaction zone or partially or substantially completely admixed. With both catalysts being homogeneous, they can be separately introduced into the reaction zone, and the point of introduction may be to the same or different regions of the reaction zone. Hence the reaction zone could have substantially uniform concentration of the catalysts throughout or could have a region containing the first catalyst and essentially none of the second catalyst. In the latter case, the relative ratio of the first and second catalyst would change in downstream regions of the reaction zone as the second catalyst is introduced. Where one catalyst is homogeneous and the other is heterogeneous, the density of each catalyst can be the same throughout the reaction zone or regions in the reaction zone can be provided with less, or no, heterogeneous catalyst.

In the continuous processes, a raw material is continuously or intermittently introduced into the reaction zone which contains a medium. A raw material, which may be one or more reactants to produce the chemical product, can be the predominant component of the medium. Alternatively, a substantially inert material can be the predominant component of the medium. The medium, where a substantially inert material is the predominant component of the medium, can be provided by separately feeding the inert material to the reaction zone or by feeding at least a portion of the inert material in combination with a raw material. Where an inert material is used to form the medium, it can be in the gas phase as it passes through the reaction zone or it can be in the liquid phase. In some instances, the inert material is a solvent for at least one of any homogeneous catalyst, one or more of the raw materials, intermediates, and chemical product. The media can serve as a fluid to suspend one or more of the catalysts such as with a fluidized bed or ebulating bed reactor.

The medium flowing through the reaction zone can be liquid, gas, or mixed gas and liquid. Where mixed gas and liquid, the gas or the liquid can be the continuous phase. Where a homogeneous catalyst is used, a liquid phase would contain the homogeneous catalyst and the liquid phase can be the continuous or gas phase the continuous phase. In some instances, the catalytic conversions can provide a chemical product in a different phase under the reaction conditions than the feed to the reaction zone or a raw material in either the gas phase of liquid phase is converted reducing the amount of that phase. In such instances, the nature of the gas and liquid phase of the flow through the reaction zone may change such that the other phase becomes the continuous phase.

As stated above, the methods for operating the processes use process parameter inputs of (I) the rate and concentration of feed of raw material in step (i) and the conversion efficiency of the raw material to the chemical product and at least one of (II) concentration of at least one by-product in the withdrawn medium, concentration of intermediate in the withdrawn medium and, if used, concentration of at least one tracer in the withdrawn medium. One of the advantages of the methods of this invention is that the data required for the process parameter inputs do not require compositional analyses inside the reaction zone.

Where the raw material comprises more than one reactant, either the manipulative input can cause each of the reactants to be supplied in a predetermined relationship to each other or the manipulative input can separately address each of the reactants or the manipulative input can address only one or less than all the reactants. For example, where the process being controlled is a hydrogenation, the manipulative input might only be with respect to the reactant being hydrogenated which reactant would be the production-limiting raw material.

As a general principle, the disclosed methods involve determining and responding to changes in the performance of one or both catalysts and the balance between their performances. Accordingly, it is not so important that the process parameter inputs be accurate as it is that changes are accurately detected. Analytical instrumentation to provide the data for the process parameter inputs is within the routine expertise of the artisan and will be dependent upon the process, the equipment configuration, the conditions used and the components present in the feeds, in the reaction zone and in the chemical product. The instrumentation can be used to determine, for instance, flow rate, composition, temperature, pressure, density, pressure, electrochemical potential, and turbidity. Examples of analytical equipment include in-line equipment and remote equipment used to analyze samples removed from the reaction zone such as, but not limited to, gas chromatographs, liquid chromatographs, IR spectrometers, nuclear magnetic resonance spectrometers, mass spectrometers, Raman spectrometers, colorimetric techniques, and titration. Examples of flow meters include, but are not limited to, orifice meters, flow nozzle meters, venture meters, rotameters, pitot tubes, turbine meters, vortex meters, electromagnetic meters, Doppler meters, ultrasonic meters, positive displacement meters, thermal mass flow meters, and Coriolis meters. The process parameter inputs are often obtained through calculations from data from the analyzers and flow meters and such calculations can be conducted manually or by machine.

The rate and concentration of feed of raw material in step (i) is based upon the raw material that is supplied at a rate which defines the stoichiometric maximum amount of intermediate that can be produced (i.e., the production-limiting raw material). By way of explanation and not in limitation, if the process involves reacting one mole of A with one mole of B, the production-limiting raw material is the raw material that is provided in the lowest molar amount. This raw material is also used for determining conversion efficiency. Where multiple raw materials are used, process parameter inputs for each raw material can still be used in accordance with the disclosed methods even though only one is used as the manipulative input. However, in some instances, the process parameter input for one raw material is sufficient for commercial processes.

The rate of feed of a raw material can be in mass, volume, molar or the like units per unit time from which conversion efficiency can be directly or indirectly calculated. Where the feed is introduced intermittently, the rate of feed can be determined either during the duration that the feed is supplied or over a predetermined time that provides an average rate or both. It should also be recognized that the rate of feed need not be constant but can cycle. Thus, where there is an adjustment of the rate of feed of the raw material to the reaction zone in response to catalyst performance changes, the rate can be an adjustment in one or more of the duration of the intermittent introduction, the frequency of intermittent introduction, and the rate that raw material is being introduced during an intermittent introduction.

The concentration of feed of raw material is the concentration of the raw material in the medium to contact the first catalyst and thus includes any components contained in the raw material such as solvents, impurities, and diluents as well as any portion of the medium introduced separately. In some instances, the rate of medium flow to the first catalyst varies very little, and hence in those instances, it can be sufficient to assume a predetermined rate of medium flow.

The withdrawn medium from the reaction zone is typically the intermittent or continuous stream passing from the reaction zone. The medium withdrawn from the reaction zone can be a single stream or may be divided into two or more aliquot streams, any of which can be used to determine concentrations of components. In some instances where the reactor design is such that the medium in the reaction zone is substantially the same as that being withdrawn, e.g., such as in a CSTR, the concentration of at least one of the by-product, intermediate, or tracer, as well as the concentration of the chemical product for determining conversion efficiency, can be determined from samples of medium from the reaction zone. It should be understood that ascertaining the concentration of a component can be used to determine the amount of that component in a stream of a known volume. Hence, even if the process parameter input is an absolute amount of catalytically active species of a component in the withdrawn stream, it is tantamount to the concentration.

The process parameter inputs used in accordance with the methods of this invention form the basis for ascertaining changes in catalyst performance that require process input adjustment to meet process objectives. It should be recognized that additional process parameter inputs can be used if desired and, in some instances, these inputs can improve the detection (quantitatively or qualitatively) of catalyst changes. The methods of this invention are broadly applicable to chemical processes using sequential catalytic reactions. Once understanding the principles of this invention and the nature of the particular process to which the methods are to be applied, it is well within the skill of an ordinary control engineer to select the process parameter inputs to be used including those process parameter inputs of (I) and (II) to establish set points, operating windows or control algorithms to adjust at least one of: (I) the absolute amount of catalytically active species and relative amounts of each of the first catalyst and second catalyst, and (II) at least one of the rate of feed of the raw material and its concentration to the reaction zone to reflect changes in catalysts and achieve process objectives.

By way of example and not in limitation of the invention, the following discusses the various process parameter inputs and their relationship to evaluating the performance of the catalysts.

The rate and concentration of feed of raw material in step (i) and the conversion efficiency of the raw material to the chemical product are important to understand the overall effectiveness of the catalysts in the reaction zone but provide no definitive information of the cause of a change in conversion efficiency. However, this information is relevant to the stress placed on the catalysts. An increase in raw material feed or increase in flow rate can each be expected to result in a sacrifice in conversion efficiency, all else being the same. One can ascertain whether a conversion efficiency decrease is consistent with a change being observed in raw material feed and/or flow rate of the medium. If the change is greater than that expected, then additional process parameter inputs are consulted to ascertain whether that change is due to a change in catalyst activity. In some instances, even if there is no change in conversion efficiency and the conversion efficiency is at values expected with a given rate of raw material feed and medium flow rate, one or both of the catalysts can be suffering from a performance change. For instance, a catalyst may be present in an amount in excess of that required. As that catalyst has a change in activity, because the catalyst is in an excess, the conversion efficiency may not change until further deterioration occurs.

At least one of concentration of at least one by-product in the withdrawn medium, concentration of intermediate in the withdrawn medium and, if used, concentration of at least one tracer in the withdrawn medium serve as process parameters that can provide, in combination with the conversion efficiency, information as to the performance of the catalysts. Especially with the model predictive control systems, the concentration of one or more by-product in the withdrawn medium, concentration of intermediate in the withdrawn medium and, if used, concentration of at least one tracer, can be used to construct the model, but need not be used once the model is constructed. The use of a tracer precursor can be continuous or intermittent. For instance, the tracer precursor can be used intermittently to assure that the process is performing as desired or to assist in troubleshooting a problem in the operation of the process and to bring the process back into alignment with desired operation.

In some catalytic processes, the amount of a by-product produced can be elucidating, especially where the by-product or reaction product thereof is produced either (i) by further reaction of the raw material or intermediate either non-catalytically or over the first catalyst or (ii) by catalytic reaction of the raw material over the second catalyst. For example, if the by-product is from the first catalyst, an increase is indicative that the second catalyst has less activity density in the reaction zone and the raw material or intermediate have additional time to enter into a reaction to form the by-product. Alternatively, if the by-product is produced via reaction of raw material over the second catalyst, an increase, all else being substantially the same, is indicative that the activity density of the first catalyst has decreased and more raw material is thus contacting the second catalyst. In some instances, a by-product is produced by the first catalyst and is further catalytically reacted to another reaction product by the second catalyst. An increase in either the by-product due to an absence of the second reaction, or a decrease in the another reaction product, all else being substantially the same, is indicative of a decrease in catalytic activity of the second catalyst.

In some catalytic processes, changes in the concentration of the intermediate in the withdrawn medium is useful. An increase is indicative of a decrease in catalytic activity of the second catalyst. The usefulness of this process parameter is limited where the intermediate is quickly reacted either catalytically or non-catalytically to chemical product or by-product and is thus not present to any extent in the withdrawn medium.

As an alternative or in addition, a tracer precursor can be used. The tracer precursor is substantially only reacted with one of the catalysts. The tracer precursor is added to the medium in a known amount and the concentration of at least one of the unreacted tracer precursor or the reaction product(s) thereof is determined in the withdrawn medium. A change in the concentration of the tracer is indicative of a change in catalytic activity. The selection of the tracer precursor will be dependent upon the reaction system and the catalysts. In some instances, the tracer precursor can be less reactive under the reaction conditions than the raw material (first catalyst) or intermediate (second catalyst). The decrease in reactivity can be due to one or more of steric effects or reactive groups that are chemically less reactive than those of the raw material or intermediate, as the case may be. The concentration of tracer precursor can vary widely and will depend upon, for instance, the ability to analytically detect the concentration of the tracer or reaction product in the withdrawn medium. Often the concentration of the tracer precursor is in the range of between about 1 part per million to 1 percent, by mass based upon mass of the medium.

In response to a detected change in catalyst activity, an adjustment is made to at least one of: (I) the absolute amount of catalytically active species and relative amounts of each of the first catalyst and second catalyst, and (II) at least one of the rate of feed of the raw material and its concentration to the reaction zone. Prior to making a change in either (I) or (II), it is usually advisable that a determination as to whether a mechanical failure or other physical event occurred that permitted maldistribution of the catalyst or other catastrophic event has not occurred.

Adjustments in the absolute amount of catalytically active species and relative amounts of the catalysts can be effected, for instance, by the addition of a catalyst or the removal of a catalyst from the reaction zone. The manner of addition or removal of catalyst is well within the skill of the art. The optimal techniques will dependent upon the type of reaction system. For example, where a homogeneous catalyst or suspended catalyst is used, catalyst can be withdrawn from the reaction zone with the medium or via recycling side streams to reduce the amount of that catalyst. Addition of catalyst can be effected by introducing catalyst to the reaction zone.

The absolute amount of catalytically active species of a catalyst can also be adjusted by treatment of the catalyst or its environment and/or by ameliorating the problem of maldistribution of the catalyst in the reaction zone. The absolute amount of catalytically active species of a catalyst is based on the effectiveness of the catalyst, not simply the overall mass of the catalyst. Thus, physical and environmental process conditions such as maldistribution and in situ catalyst conditions that cause catalyst loss such as coating, poisoning, sintering, loss of catalytic species due to solubilization, and steric effects or reactions or complexing with the raw material or intermediate are reflected in absolute amount of catalytically active species available for a reaction. For instance, the formation of deposits on a catalyst reduces the available catalyst sites. Removing all or a portion of the deposits increases the number of available catalyst sites and thus is an increase in the absolute amount of catalytically active species of catalyst. In some instances, the catalytic species in a catalyst becomes oxidized or reduced. For example, nickel used in a hydrogenation catalyst can become oxidized and no longer be catalytically active. Reducing the oxidized nickel would increase the amount of nickel catalytically available and thus would result in an increase in the absolute amount of catalytically active species of catalyst. Similarly, a catalytic species may be oxidized or reduced or converted to a more or less active species. This is particularly the case where the catalytic species is a complex or can form a complex.

In addition or alternatively, the adjustment to accommodate a change in catalytic activity can be a change in the rate of supply of raw material. The raw material feed rate would thus take into account that at least one of the catalysts in the reaction zone provides less catalytically active species. However, the production rate of the chemical product would also be decreased. In some instances, a change in raw material feed rate and rate of flow of the medium, an increase in a by-product occurs. Where the process objective is to minimize formation of that by-product, the adjustment in raw material feed rate and rate of flow of the medium, may effect a compromise.

The methods of this invention are broadly applicable to sequential catalytic processes that are capable of being conducted in a single reaction zone. Thus, the processes can be to make chemicals, pharmaceuticals, and fuels. The methods of this invention can use raw materials and catalysts of the type used for such processes when operated in a modulated manner.

One application of the methods of this invention is to processes for the conversion of carbohydrate that contains an aldohexose-yielding carbohydrate or ketose-yielding carbohydrate to at least one of ethylene glycol and propylene glycol (lower glycol) in a reaction zone are effected by subjecting the sugar to catalytic retro-aldol conditions to produce an intermediate that is hydrogenated under catalytic hydrogenation conditions. See, for instance, U.S. published patent applications 2017/0349513 and 2018/0086681 and U.S. Pat. Nos. 9,399,610 and 9,783,472, all hereby incorporated by reference in their entireties.

The raw material comprises carbohydrate which is most often at least one of pentose and hexose or compounds that yield pentose or hexose. Examples of pentose and hexose include xylose, lyxose, ribose, arabinose, xylulose, ribulose, glucose, mannose, galactose, allose, altrose, idose, talose, and gulose fructose, psicose, sorbose, and tagatose. Most bio-sourced carbohydrate feedstocks yield glucose upon being hydrolyzed. Glucose precursors include, but are not limited to, maltose, trehalose, cellobiose, kojibiose, nigerose, nigerose, isomaltose, β,β-trehalose, α,β-trehalose, sophorose, laminaribiose, gentiobiose, and mannobiose. Carbohydrate polymers and oligomers such as hemicellulose, partially hydrolyzed forms of hemicellulose, disaccharides such as sucrose, lactulose, lactose, turanose, maltulose, palatinose, gentiobiulose, melibiose, and melibiulose, or combinations thereof may be used.

In these processes, an aqueous medium containing the carbohydrate is contacted with retro-aldol catalyst under retro-aldol reaction conditions. The contact may commence prior to or upon introducing the aqueous medium into a hydrogenation catalyst-containing portion of the reaction zone. The preferred temperatures for retro-aldol reactions are typically from about 230° C. to 300° C., and more preferably from about 240° C. to 280° C., although retro-aldol reactions can occur at lower temperatures, e.g., as low as 90° C. or 150° C. The pressures (absolute) are typically in the range of about 15 to 200 bar (1500 to 20,000 kPa), say, from about 25 to 150 bar (2500 to 15000 kPa).

Retro-aldol reaction conditions include the presence of retro-aldol catalyst. A retro-aldol catalyst is a catalyst that catalyzes the retro-aldol reaction. Examples of compounds that can provide retro-aldol catalyst include, but are not limited to, heterogeneous and homogeneous catalysts, including catalyst supported on a carrier, comprising tungsten and its oxides, sulfates, phosphides, nitrides, carbides, halides, acids and the like. Tungsten carbide, soluble phosphotungstens, tungsten oxides supported on zirconia, alumina and alumina-silica are also included. Preferred catalysts are provided by soluble tungsten compounds and mixtures of tungsten compounds. Soluble tungstates include, but are not limited to, ammonium and alkali metal, e.g., sodium and potassium, paratungstate, partially neutralized tungstic acid, ammonium and alkali metal metatungstate and ammonium and alkali metal tungstate. Often the presence of ammonium cation results in the generation of amine by-products that are undesirable in the lower glycol product. Without wishing to be limited to theory, the species that exhibit the catalytic activity may or may not be the same as the soluble tungsten compounds introduced as a catalyst. Rather, a catalytically active species may be formed as a result of exposure to the retro-aldol reaction conditions. Tungsten-containing complexes are typically pH dependent. For instance, a solution containing sodium tungstate at a pH greater than 7 will generate sodium metatungstate when the pH is lowered. The form of the complexed tungstate anions is generally pH dependent. The rate that complexed anions formed from the condensation of tungstate anions are formed is influenced by the concentration of tungsten-containing anions. A preferred retro-aldol catalyst comprises ammonium or alkali metal tungstate that becomes partially neutralized with acid, preferably an organic acid of 1 to 6 carbons such as, but without limitation, formic acid, acetic acid, glycolic acid, and lactic acid. The partial neutralization is often from about 25 to 75%, i.e., on average from 25 to 75% of the cations of the tungstate become acid sites. The partial neutralization may occur prior to introducing the tungsten-containing compound into the reactor or with acid contained in the reactor.

The concentration of retro-aldol catalyst used may vary widely and will depend upon the activity of the catalyst and the other conditions of the retro-aldol reaction such as acidity, temperature and concentrations of carbohydrate. Typically, the retro-aldol catalyst is provided in an amount to provide from about 0.01 or 0.05 to 100, say, from about 0.02 or 0.1 to 50, grams of tungsten calculated as the elemental metal per liter of aqueous, hydrogenation medium. The retro-aldol catalyst can be added as a mixture with all or a portion of the carbohydrate feed or as a separate feed to the aqueous, hydrogenation medium or with recycling aqueous medium or any combination thereof. In some instances, a homogeneous, tungsten-containing retro-aldol catalyst can deposit a tungsten-containing compound or complex on the hydrogenation catalyst and adversely affect the activity of the hydrogenation catalyst. A continuous or intermittent cycling of the amount of tungsten-containing catalyst can result in removal of at least a portion of the deposited tungsten compound or complex. The disclosed methods thus contemplate that the control of the absolute amount of catalytically active species and relative amounts of each of the first catalyst and second catalyst includes operations where the process objective is a rejuvenation of a catalyst.

Frequently the carbohydrate feed is subjected to retro-aldol conditions prior to being introduced into the aqueous, hydrogenation medium in the reaction zone containing hydrogenation catalyst. Preferably the introduction into the aqueous, hydrogenation medium occurs in less than one minute, and most often less than 10 seconds, from the commencement of subjecting the carbohydrate feed to the retro-aldol conditions. Some, or all of the retro-aldol reaction can occur in the reaction zone containing the hydrogenation catalyst. In any event, the most preferred processes are those having a short duration of time between the retro-aldol conversion and hydrogenation.

The hydrogenation, that is, the addition of hydrogen atoms to an organic compound without cleaving carbon-to-carbon bonds, can be conducted at a temperature in the range of about 100° C. or 120° C. to 300° C. or more. Typically, the aqueous, hydrogenation medium is maintained at a temperature of at least about 230° C. until substantially all carbohydrate is reacted to have the carbohydrate carbon-carbon bonds broken by the retro-aldol reaction, thereby enhancing selectivity to ethylene and propylene glycol. Thereafter, if desired, the temperature of the aqueous, hydrogenation medium can be reduced. However, the hydrogenation proceeds rapidly at these higher temperatures. Thus, the temperatures for hydrogenation reactions are frequently between about 230° C. and 300° C., say, between about 240° C. and 280° C. The pressures are typically in the range of about 15 to 200 bar, say, from about 25 to 150 bar. The hydrogenation reactions require the presence of hydrogen as well as hydrogenation catalyst. Hydrogen has low solubility in aqueous solutions. The concentration of hydrogen in the aqueous, hydrogenation medium is increased with increased partial pressure of hydrogen in the reaction zone. The pH of the aqueous, hydrogenation medium is often at least about 3, say, from about 3 or 3.5 to 8, and in some instances from about 3.2 or 4 to 7.5.

The hydrogenation is conducted in the presence of a hydrogenation catalyst. Frequently the hydrogenation catalyst is a heterogeneous catalyst. It can be deployed in any suitable manner, including, but not limited to, fixed bed, fluidized bed, trickle bed, moving bed, slurry bed, and structured bed. Nickel, ruthenium, palladium and platinum are among the more widely used reducing metal catalysts. However, many reducing catalysts will work in this application. The reducing catalyst can be chosen from a wide variety of supported transition metal catalysts. Nickel, Pt, Pd and ruthenium as the primary reducing metal components are well known for their ability to reduce carbonyls. One particularly favored catalyst for the reducing catalyst in this process is a supported, Ni—Re catalyst. A similar version of Ni/Re or Ni/Ir can be used with good selectivity for the conversion of the formed glycolaldehyde to ethylene glycol. Nickel-rhenium is a preferred reducing metal catalyst and may be supported on alumina, alumina-silica, silica or other supports. Supported Ni—Re catalysts with B as a promoter are useful. Generally, for slurry reactors, a supported hydrogenation catalyst is provided in an amount of less than 10, and sometimes less than about 5, say, about 0.1 or 0.5 to 3, grams per liter of nickel (calculated as elemental nickel) per liter of liquid medium in the reactor. As stated above, not all the nickel in the catalyst is in the zero-valence state, nor is all the nickel in the zero-valence state readily accessible by glycol aldehyde or hydrogen. Hence, for a particular hydrogenation catalyst, the optimal mass of nickel per liter of liquid medium will vary. For instance, Raney nickel catalysts would provide a much greater concentration of nickel per liter of liquid medium. Frequently in a slurry reactor, the hydrogenation catalyst is provided in an amount of at least about 5 or 10, and more often, from about 10 to 70 or 100, grams per liter of aqueous, hydrogenation medium and in a packed bed reactor the hydrogenation catalyst comprises about 20 to 80 volume percent of the reactor. In some instances, the weight hourly space velocity is between about 0.01 or 0.05 and 1 hr-1 based upon total carbohydrate in the feed. Preferably the residence time is sufficient that glycol aldehyde and glucose are less than 0.1 mass percent of the reaction product, and most preferably are less than 0.001 mass percent of the reaction product.

The carbohydrate feed is at least 50 grams of carbohydrate per liter per hour, and is often in the range of about 100 to 700 or 1000, grams of carbohydrate per liter per hour. In the processes of this invention, the combination of reaction conditions (e.g., temperature, hydrogen partial pressure, concentration of catalysts, hydraulic distribution, and residence time) are sufficient to convert at least about 95, often at least about 98, mass percent and sometimes essentially all of the carbohydrate that yield aldose or ketose. It is well within the skill of the artisan having the benefit of the disclosure herein to determine the set or sets of conditions that will provide the sought conversion of the carbohydrate.

In the methods of this invention applied to the retro-aldol/hydrogenation process for making lower glycol, a process parameter input is preferably the concentration in the withdrawn medium of at least one of itol, 1,2-butanediol, and hydroxyacetone. The itols contained in the withdrawn medium result from reactions with the carbohydrate feed. Glucose, for instance, can be hydrogenated to sorbitol. In the retro-aldol step, glucose can provide glycol aldehyde and erythrose and threose. These four carbon sugars, when hydrogenated, produce erythritol and threitol. Glucose can also undergo isomerization to fructose, and fructose, when hydrogenated, go to mannitol. Also, fructose under retro-aldol conditions, goes to three carbon compounds and thus glycerol can be produced. Because of the genesis of the itols, insights into the process can be obtained from the type and the rate of production of the itols. Where a tracer precursor is used, it preferably is a ketone, e.g., a ketone of 3 to 10 carbons.

As a general matter, an increase in itol concentration, all other things remaining substantially constant, is indicative that the first catalyst has suffered a loss of catalytically active species, and one example of a manipulative inputs would be an adjustment to at least one of (I) the absolute amount and relative amounts of each of the retro-aldol catalyst and hydrogenation catalyst by increasing the catalyst activity of the retro-aldol catalyst or decreasing the catalyst activity of the hydrogenation catalyst, and (II) reducing the rate of feed of the raw material to the reaction zone.

If 1,2-butanediol concentration is used as a process parameter input, the 1,2-butanediol can result from the reaction between two glycolaldehyde molecules or from the dehydration of a tetrose. In the former, the general rule is that an increase in the 1,2-butanediol concentration is reflecting a loss of hydrogenation catalyst activity in the reaction zone, all other things remaining substantially the same. In this case, an example of an adjustment of manipulative inputs would be to at least one of (I) the absolute amount and relative amounts of each of the retro-aldol catalyst and hydrogenation catalyst by increasing the catalyst activity of the hydrogenation catalyst or decreasing the catalyst activity of the retro-aldol catalyst, and (II) reducing the rate of feed of the raw material to the reaction zone. In the latter, the retro-aldol conversion activity is likely inadequate, and (I) increasing activity of the retro-aldol catalyst, and (II) at least one of reducing the rate of feed of the raw material and its concentration to the reaction zone, would be responsive actions. Thus, having another parameter to directionally indicate whether the change in concentration of 1,2-butanediol can be helpful. For example, if an increase in 1,2-butanediol is accompanied by an increase in glycerin, which is made from fructose, which is from the isomerization of glucose, would be indicative of a reduction in retro-aldol activity since the isomerization reaction is out pacing the retro-aldol conversions, all else remaining the same.

Hydrogenation catalyst can lose activity for a number of reasons, including, but not limited to, deposits occluding catalytic sites, loss of catalytic metal due to, for instance, oxidation or solubilization, and sintering of the catalytic metal. The disclosed methods contemplate that in some instances, hydrogenation catalyst is withdrawn from the reaction zone and at least partially replaced with fresh or rejuvenated hydrogenation catalyst as a means to adjust the catalyst activity of the hydrogenation catalyst. The control methods can control the rate, both in terms of frequency and mass, of hydrogenation catalyst withdrawn and replenished to the reaction zone to maintain hydrogenation activity within a desired range.

Optimizing the retro-aldol process to make ethylene glycol involves optimizing the retro-aldol conversion, which is primarily kinetic limited, and the hydrogenation reaction which is primarily mass transfer limited. Mass transfer limitations include the supply of hydrogen to the hydrogenation catalytic sites, and hydrogen starvation can occur where localized regions of high hydrogenation catalytic active exist. The hydrogen starvation can be caused by, by way of example and not in limitation, maldistribution of the hydrogenation catalyst within the reaction zone and localized regions of higher feed concentration in the reaction zone. Hydrogen starvation thus can result in the formation of organic acids, and organic acids are by-products in the withdrawn medium and thus can be used in the processes of this invention. For purposes of process control, pH determinations can often be used as a proxy for organic acid concentration. In some instances, reducing the rate of feed can attenuate the generation of acids; however, manipulation of one or both of the absolute amount and relative amounts of retro-aldol catalyst and hydrogenation catalyst may also be required.

Hydroxyacetone is usually present in the withdrawn medium in a very low concentration. It has been found, however, to be a sensitive indicator of a decrease in activity of the hydrogenation catalyst. An increase in hydroxyacetone concentration can be addressed by increasing the catalytic activity of the hydrogenation catalyst and/or reducing the rate of raw material feed to the reaction zone. In some instances, the hydroxyacetone concentration in the withdrawn medium is less than 0.15 mass percent, preferably less than 0.10 mass percent.

A tracer can be used similarly to hydroxyacetone. Ketones such as methyl ethyl ketone can be useful tracer precursors for the retro-aldol/hydrogenation process as the internal carbonyl is more resistant to hydrogenation than the carbonyl of an aldehyde. The extent of hydrogenation of the ketone is thus an indicator of the hydrogenation activity in the reaction zone.

Although the disclosure has been described with references to various embodiments, persons skilled in the art will recognized that changes may be made in form and detail without departing from the spirit and scope of this disclosure.

What is claimed is:

1. A model predictive control method for operating a continuous, unmodulated, sequential, multi-catalytic reaction process wherein each catalyst is subject to changes in performance in the course of the process, the catalytic reaction process comprising:
   (i) continuously or intermittently introducing at a feed rate at least one raw material, and optionally a tracer precursor, into a reaction zone containing a medium, wherein the medium is a liquid medium, and wherein the at least one raw material includes a carbohydrate and the tracer precursor is a ketone of 3 to 10 carbons,
   (ii) maintaining the reaction zone under catalytic conversion conditions suitable for a first catalytic conversion to produce a medium containing an intermediate, said conditions including temperature, pressure, residence time, concentration of the first catalyst providing catalytically active species, and, optionally, pH and adjuvants,
   (iii) contacting the medium containing the intermediate with a second catalyst providing catalytically active species under conditions suitable for the other conversion to produce a chemical product, said conditions including temperature, pressure, residence time, concentration of the second catalyst, and, optionally, pH and adjuvants, wherein the chemical product is at least and the tracer precursor is a ketone of 3 to 10 carbons; and
   (iv) continuously or intermittently withdrawing medium containing the chemical product from contact with the second catalyst at a rate to provide a continuous process;
   wherein at least one byproduct is produced, and wherein the catalytic activity of at least one of the first catalyst and second catalyst is subject to performance change during the continuous operation,
said control method comprising:
   (a) continuously or intermittently inputting predetermined process parameters from the process operation into a model predictive control apparatus having a control model;
   (b) adjusting, as necessary to meet a desired process objective, manipulative inputs to the process; and, optionally
   (c) adjusting the control model,
wherein:
   (A) in element (a) the predetermined process parameters inputted comprise (I) the rate and concentration of feed of raw material in step (i) and the conversion efficiency of the raw material to the chemical product and (II) at least one of concentration of at least one:
      by-product in the withdrawn medium,
      concentration of intermediate in the withdrawn medium and
      concentration of at least one tracer in the withdrawn medium
   to reflect in control model data pertaining to the performances of the catalysts; and
   (B) in element (b) adjusting, as necessary to meet a desired process objective, at least one of: (I) the absolute amount of catalytically active species and relative amounts of each of the first catalyst and second catalyst, and (II) at least one of the rate of feed of the raw material and its concentration to the reaction zone as manipulative inputs.

2. The method of claim 1 wherein at least one of the first catalyst and the second catalyst are homogeneous.

3. The method of claim 1 wherein the reaction zone comprises two vessels in flow sequence.

4. The method of claim 1 wherein the adjustment of the absolute amount of catalytically active species of at least one of the catalysts is by addition of an additional amount of said catalyst to the reaction zone.

5. The method of claim 1 wherein the adjustment of the absolute amount of catalytically active species of at least one of the catalysts is by modulating the effectiveness of the catalyst in the reaction zone.

6. The method of claim 1 wherein the reaction zone is a single pot reaction zone.

7. The method of claim 1 wherein the process is for converting the carbohydrate to lower glycol of at least one of ethylene glycol and propylene glycol by sequential retro-aldol catalysis of carbohydrate to produce intermediates and hydrogenation catalysis of intermediates to the lower glycol.

8. The method of claim 7 wherein a concentration of at least one of a 1,2-butane diol, propylene glycol, at least one of an itol, hydroxyacetone and tracer in the withdrawn medium are used to reflect performances of the catalysts.

9. The method of claim 8 wherein the itol is one or more of erythritol, threitol, glycerin, mannitol, and sorbitol.

10. A method for operating a continuous, unmodulated, sequential, multi-catalytic reaction process wherein each catalyst is subject to changes in performance in the course of the process, which methods adjust manipulative inputs to provide outputs within predetermined ranges, the catalytic reaction process comprising:
   (i) continuously or intermittently introducing at a feed rate and concentration at least one raw material, and optionally a tracer precursor, into a reaction zone containing liquid medium, wherein the at least one raw material includes a carbohydrate and the tracer precursor is a ketone of 3 to 10 carbons,
   (ii) maintaining the reaction zone under catalytic conversion conditions suitable for a first catalytic conversion to produce a liquid medium containing an intermediate, said conditions including temperature, pressure, residence time, concentration of the first catalyst providing catalytically active species, and, optionally, pH and adjuvants,
   (iii) contacting the liquid medium containing the intermediate with a second catalyst providing catalytically active species under conditions suitable for the other conversion to produce the chemical product, said conditions including temperature, pressure, residence time, concentration of the second catalyst, and, optionally, pH and adjuvants, wherein the chemical product is at least and the tracer precursor is a ketone of 3 to 10 carbons, and
   (iv) continuously or intermittently withdrawing liquid medium containing chemical product from contact with the second catalyst at a rate to provide a continuous process;
   wherein at least one byproduct is produced, and wherein the catalytic activity of at least one of the first catalyst and second catalyst is subject to performance change during the continuous operation,
the method comprises:
   (a) continuously or intermittently comparing predetermined process parameters from the process operation to predetermined windows for such operation; and
   (b) adjusting, as necessary to meet a desired process objective, manipulative inputs to the process,
wherein in element (a) the predetermined process parameters inputted comprise (I) the rate and concentration of feed of raw material in step (i) and the conversion efficiency of the raw material to the chemical product and (II) at least one of concentration of at least one by-product in the withdrawn liquid medium, concentration of intermediate in the withdrawn liquid medium and, if used, concentration of at least one tracer in the withdrawn liquid medium, and wherein in element (b) adjustment is made to at least one of: (I) the absolute amount of catalytically active species and relative amounts of each of the first catalyst and second catalyst, and (II) at least one of the rate of feed and concentration of the raw material to the reaction zone as the manipulative inputs.

11. The method of claim 10 wherein at least one of the first catalyst and the second catalyst are homogeneous.

12. The method of claim 10 wherein the reaction zone comprises two vessels in flow sequence.

13. The method of claim 10 wherein the adjustment of the absolute amount of catalytically active species of at least one of the catalysts is by addition of an additional amount of said catalyst to the reaction zone.

14. The method of claim 10 wherein the adjustment of the absolute amount of catalytically active species of at least one of the catalysts is by modulating the effectiveness of the catalyst in the reaction zone.

15. The method of claim 10 wherein the reaction zone is a single pot reaction zone.

16. The method of claim 10 wherein the process is for converting the carbohydrate to lower glycol of at least one of ethylene glycol and propylene glycol by sequential retro-aldol catalysis of carbohydrate to produce intermediates and hydrogenation catalysis of intermediates to the lower glycol.

17. The method of claim 16 wherein a 1,2-butane diol, propylene glycol, at least one itol, hydroxyacetone, pH and tracer in the withdrawn medium are used to reflect performances of the catalysts.

18. The method of claim 17 wherein the itol is one or more of erythritol, threitol, glycerin, mannitol, and sorbitol.

* * * * *

UNITED STATES PATENT AND TRADEMARK OFFICE
CERTIFICATE OF CORRECTION

PATENT NO.            : 11,919,840 B2
APPLICATION NO.       : 17/031009
DATED                 : March 5, 2024
INVENTOR(S)           : Ray Chrisman et al.

Page 1 of 1

It is certified that error appears in the above-identified patent and that said Letters Patent is hereby corrected as shown below:

In the Claims

Column 20, Lines 31-33, in Claim 1, change "wherein the chemical product is at least and the tracer precursor is a ketone of 3 to 10 carbons" to --wherein the chemical product is at least one of ethylene glycol and propylene glycol and the tracer precursor is a ketone of 3 to 10 carbons--

Column 21, Lines 54-56, in Claim 10, change "wherein the chemical product is at least and the tracer precursor is a ketone of 3 to 10 carbons" to --wherein the chemical product is at least one of ethylene glycol and propylene glycol and the tracer precursor is a ketone of 3 to 10 carbons--

Signed and Sealed this
Ninth Day of September, 2025

Coke Morgan Stewart
*Acting Director of the United States Patent and Trademark Office*